United States Patent [19]

Roman

[11] 4,044,128
[45] Aug. 23, 1977

[54] INSECTICIDAL SULFONIUM SALTS
[75] Inventor: Steven A. Roman, Oakdale, Calif.
[73] Assignee: Shell Oil Company, Houston, Tex.
[21] Appl. No.: 694,748
[22] Filed: June 10, 1976

Related U.S. Application Data

[63] Continuation-in-part of Ser. No. 582,578, June 2, 1975, abandoned, which is a continuation-in-part of Ser. No. 468,125, May 8, 1974, abandoned.

[51] Int. Cl.$^2$ .................... C07D 279/04; A01N 9/12
[52] U.S. Cl. ...................................... 424/246; 544/54
[58] Field of Search .................... 260/243 R; 424/246

[56] References Cited
U.S. PATENT DOCUMENTS

| 3,098,071 | 7/1963 | Blatter et al. | 260/243 |
| 3,131,183 | 4/1964 | Hoffmann et al. | 260/243 |

Primary Examiner—Leonard Schenkman

[57] ABSTRACT

Novel insecticidal sulfonium salts of 2-(alkylthio)ethyl esters of alpha-nitro-alpha(tetrahydro-2H-1,3-thiazin-2-ylidene)acetic acids.

5 Claims, No Drawings

INSECTICIDAL SULFONIUM SALTS

This application is a continuation-in-part of copending application Ser. No. 582,578, filed June 2, 1975, now abandoned, which is a continuation-in-part of application Ser. No. 468,125, filed May 8, 1974, now abandoned.

BACKGROUND TO THE INVENTION

U.S. Pat. No. 3,962,234 discloses and claims certain insecticidal esters of nitro(tetrahydro-2H-1,3-thiazin-2-ylidene)acetic acids, of the general formula

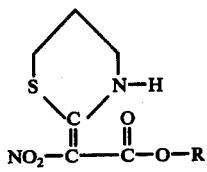

wherein the symbol R has a defined meaning, and salts thereof. Those insecticidal esters are characterized by particularly high insecticidal activity with respect to caterpillar forms of the genera Heliothis, Agrotis, Trichoplusia and Spodoptera.

DESCRIPTION OF THE INVENTION

It now has been found that a particular limited subclass of salts of such esters and closely related esters are of particular interest, in that they exhibit markedly higher activity to caterpillars of the indicated genera than do the corresponding esters per se. This particular class of salts is defined by the general formula:

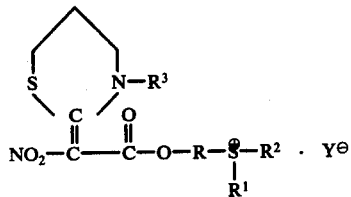

wherein Y is an anion: chloride, bromide, iodide, alkyl sulfate (alkyl—$SO_4^-$), fluorosulfonate ($FSO_3^-$) or fluoborate ($BF_4^-$), R is —$CH_2$—$CH_2$— or such in which one of the hydrogen atoms has been replaced by methyl, $R^1$ is alkyl of one to three carbon atoms, $R^2$ contains up to twenty carbon atoms and is alkyl or alkenyl, or is phenyl, benzyl or phenethyl, and $R^3$ is hydrogen or

wherein Z is —$R^4$, —$OR^4$ or —$SR^4$, $R^4$ being one of the moieties represented by $R^2$.

Preferably, the moieties represented by $R^2$ and $R^4$ contain no more than fifteen carbon atoms each and when aliphatic may be of straight-chain or branched-chain configuration.

The salts of this invention (as is the case with the corresponding esters) are resonance hybrids, and in the subclass wherein $R^3$ is hydrogen may exist in tautomeric enol forms, and all may exist as geometric isomers, as described for the esters in U.S. Pat. No. 3,962,234.

Because of their insecticidal activity characteristics, a preferred sub-genus of the genus of the invention consists of those compounds of the general formula wherein $R^1$ is methyl, $R^2$ is alkyl of from one to fifteen carbon atoms or is phenyl, $R^3$ is hydrogen, alkanoyl or alkoxycarbonyl of from one to ten carbon atoms, or is benzoyl, and Y is chloride, bromide or iodide. Optimum insecticidal activity appears to be associated with the preferred sub-class wherein $R^2$ is alkyl of from one to fifteen carbon atoms or phenyl, $R^3$ is hydrogen or benzoyl and Y is bromide or iodide.

For illustration, preparation of typical species salts of the genus is described in the examples included hereinafter. Other typical, illustrative species of this genus include those wherein the symbols represent the following moieties, this manner of naming these species being accurate, yet pointing out the differences between the different species more clearly than if the entire, complicated name of each species were to be given:

| R | $R^1$ | $R^2$ | $R^3$ | Y |
|---|---|---|---|---|
| —$CH_2$—$CH_2$— | methyl | allyl | H | I |
| —$CH_2$—$CH_2$— | methyl | methyl | acetyl | I |
| —$CH_2$—$CH_2$— | ethyl | ethyl | H | I |
| —$CH_2$—$CH_2$— | methyl | methyl | methoxycarbonyl | I |

The salts of this invention are readily prepared by treating the corresponding 2—($R^2$-thio)R esters with the appropriate compound $R^1$—Y, in a suitable solvent, at room temperature or moderately above — for example, up to 50° C.

The precursor 2—($R^2$-thio)R esters can be prepared by the base-promoted transesterification of an alkyl ester

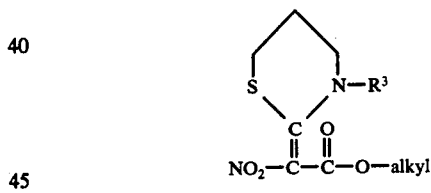

by the general procedure described in U.S. Pat. No. 3,962,234.

It will be found in some cases that it will be most convenient to use the methyl or ethyl ester.

The ester interchange follows the conventional base-promoted reaction of an ester with the alcoholate of the appropriate alcohol. According to one technique, the interchange can be effected by treating the alkyl ester with an excess of the appropriate alcohol in the presence of two equivalents of an alkali metal (one equivalent of the metal converts the alcohol to the alcoholate, while the other equivalent neutralizes the acidic ester products.) Use of a small to moderate (5–10%) excess of the metal may be effected at temperatures of about 20°–100°.

Alternatively, the metal alcoholate can be prepared and reacted with the ester in an aprotic solvent such as tetrahydrofuran. This may be done by treating the appropriate alcohol in the solvent with an alkali metal hydride, then adding the ester, also in the solvent. The reaction of the alcohol and hydride usually is exothermic so that cooling is usually needed to control the temperature of the reaction mixture. Reaction of the alcoholate with the ester ordinarily can be conducted at room temperature.

With either technique, recovery of the product is effectively attained in most cases by quenching the final reaction mixture in water, treating the aqueous mixture with a suitable solvent such as ether to remove the solvent alcohol and other neutral organic species, then acidifying the aqueous phase. In some cases, the product ester crystallizes out of the water; in other cases, it can be recovered by extracting the water-phase with a suitable water-insoluble solvent such as methylene chloride or ethyl ether.

1. Where $R^3$ is hydrogen, preparation of the necessary alkyl ester precursor is disclosed in U.S. Pat. No. 3,962,234 — as by the zinc ion-catalyzed reaction of 5,6-dihydro-2-(methylthio)-4H-1,3-thiazine (A. F. McKay et al., J. Am. Chem. Soc. 80,3339 (1950)) with an alkyl nitroacetate (S. Zen, et al., Kogyo Kagaku Zasshi, 74, 70 (1971)).

2. Where $R^3$ is

the salts of the invention can be prepared in the same way, employing the appropriate alkyl esters, which esters and their preparation are disclosed in application Ser. No. 663,317, filed Apr. 2, 1975. As shown therein, such esters are prepared from the $R^3$ is H esters described in (1) above, and in U.S. Pat. No. 3,962,234. They can be converted to the $R^3$ is

esters by treating the alkali metal (e.g., sodium) derivative of the $R^3$ is H ester with the appropriate acid chloride, chloroformate or chlorothioformate, or sulfenyl, sulfinyl or sulfonyl chloride.

The acid chloride, chloroformate, and chlorothioformate and sulfenyl chloride reactants are in many cases known compounds, and in those cases when they are specifically novel, can be prepared by the procedures known in the art for the known analogs thereof.

The thiazine precursors are converted to the needed alkali metal derivatives by treatment with an alkali metal hydride, such as sodium hydride, preferably in a suitable liquid reaction medium, such as tetrahydrofuran, at a low temperature, for example, about 0° C. To enable efficient control of the often exothermic reaction, it may be found desirable to add slowly a solution or suspension of the thiazine to a stirred, cooled solution or suspension of the base, the mixture being stirred further until hydrogen ceases to evolve. The mixture then may be allowed to warm, for example to room temperature, to ensure completion of the reaction.

Treatment of the alkali metal derivative with the carbonylic reactant can be effectively carried out under similar conditions: adding a suspension or solution of the carbonylic reactant slowly to a stirred solution or suspension of the alkali metal derivative, the reaction mixture being cooled as necessary to maintain it at a low temperature — again, suitably about 0° C — then allowing the stirred mixture to warm, for example to room temperature, and stirring the warmed mixture for a period of time to ensure complete reaction.

It often will be found convenient to employ the same liquid reaction medium in both steps of the process, with tetrahydrofuran generally being quite suitable for this purpose. In such case, the solution or suspension of the alkali metal derivative obtained as the product of the alkali metal hydride/thiazine reaction is treated directly with the solution or suspension of the carbonylic reactant.

The desired product can be isolated from the crude reaction mixture and purified by conventional methods, such as filtration, extraction, crystallization and elution (chromatography).

Preparation of the precursor also can be effected by treating the $R^3$ is H ester with the appropriate acid anhydride, in a suitable solvent, such as methylene chloride or other haloalkane, using reaction conditions and product recovery and purification techniques described above.

These procedures for preparing compounds of this invention are illustrated in the following examples of the preparation of particular species of such compounds. In all cases the identity of the precursor(s) had been established and the identity of the final product was confirmed, by appropriate chemical and spectral analyses:

EXAMPLE 1 dimethyl(2-(nitro(tetrahydro-2H-1,3thiazin-2-ylidene)acetyloxy)ethyl)sulfonium iodide (1)

A solution of 100 g of 2-(methylthio)ethanol in dry tetrahydrofuran was added slowly to a solution of 6.0 g of sodium hydride (57% in mineral oil) in dry tetrahydrofuran at 0°. The mixture was then allowed to warm to room temperature and 13.1 g of methyl nitro(tetrahydro-2H-1,3-thiazin-2-ylidene)acetate (1A), prepared as described in U.S. Pat. No. 3,962,234, was added, and the mixture was allowed to stand overnight at room temperature. The solvent then was evaporated under reduced pressure, the residue was poured into water and the mixture was extracted with ether. The separated aqueous phase was acidified with acetic acid, and the product was extracted with methylene chloride. The extract was dried (MgSO₄), decolorized, and the solvent was evaporated under reduced pressure. The residue was washed with pentane, then crystallized from ether and recrystallized from isopropyl alcohol to give the 2-(methylthio)ethyl ester of nitro(tetrahydro-2H-1,3-thiazin-2-ylidene)acetic acid (1B), as a pale yellow solid, m.p.: 72°–73°.

1.0 g of 1B mixed with 3 ml of methyl iodide in 10 ml of acetone was allowed to stand at room temperature for 24 hours. Filtration gave 1 as a pale yellow solid, m.p.: 127°–128° (with decomposition).

EXAMPLES 2 and 3

In a similar manner, the methyl sulfate salt (2) and the bromide salt (3) of 1B were prepared, as, respectively, a yellow solid, m.p.: about ambient, and as a pale yellow solid, m.p.: 130° (with decomposition).

EXAMPLES 4 and 5

Butylmethyl(2-(nitro(tetrahydro-2H-1,3-thiazin-2-ylidene)acetyloxy)ethyl)sulfonium iodide (4), and the corresponding ethylmethyl analog (5) were prepared from the corresponding 2-(butylthio)ethyl and 2-ethylthio)ethyl esters and methyl iodide, in the manner described in Examples 1-3, as, respectively, an orange liquid, b.p.: not determined, and a yellow solid, m.p.: 89°-90° (with decomposition).

EXAMPLE 6 methyl(2-(nitro(tetrahydro-2H-1,3-thiazin-2-ylidene)acetyloxy)ethyl)phenylsulfonium flurorsulfonate (6)

2 g of the 2-(phenylthio)ester of nitro(tetrahydro-2H-1,3-thiazin-2-ylidene)acetic acid (U.S. Pat. No. 3,962,234) was mixed with 0.7 g of methyl fluorosulfonate in 10 ml of methylene chloride, and the mixture was stirred at room temperature over a week-end. The solvent was decanted from an oil phase in the final mixture. The oil phase was triturated with ether and acetone, and the oil was stirred in ether overnight. The resulting solid was transferred, under ether, to a container and the ether was evaporated under reduced pressure to give 6, as an orange gummy solid.

EXAMPLE 7

(2-((3-benzoyltetrahydro-2H-1,3-thiazin-2-ylidene)nitroacetyloxy)ethyl)dimethyl sulfonium iodide (7)

1.75 g of 1B was added in portions to a slurry of 0.3 g of ether-washed sodium hydride in 25 ml of tetrahydrofuran at 0°. The stirred mixture was allowed to warm to room temperature and stirred for 20 minutes. Then 0.9 g of benzoyl chloride in 10 ml of tetrahydrofuran was added dropwise, over a 10-minute period, and the mixture was stirred overnight at room temperature. Then a few drops of water were added to decompose excess sodium hydride, the mixture was poured into water and the resulting mixture was extracted with methylene chloride. The extract phase was washed with water, dried (MgSO$_4$) and filtered, and the solvent was evaporated under reduced pressure. The residue was dissolved in ether; the solution was washed with water, dried (MgSO$_4$), and the solvent evaporated under reduced pressure to give an oil, which was dissolved in methylene chloride. The resulting solution was passed through Florisil and the solvent was evaporated under reduced pressure to give the 2-(methylthio)ethyl ester of (3-benzoyltetrahydro-2H-1,3-thiazin-2-ylidene) nitroacetic acid (7A), as a yellow liquid.

1.4 g of 7A, 6 ml of methyl iodide and 10 ml of acetone were mixed and the mixture was stirred overnight at room temperature. The solid was collected, washed with acetone, then ether, to give 7, as a yellow solid, m.p.: 115° (with decomposition).

EXAMPLE 8 methyl(2-(nitro(tetrahydro)-2H-1,3-thiazin-2-ylidene)acetyloxy)ethyl)octylsulfonium fluorosulfonate (8)

2-(octylthio)ethyl nitro(tetrahydro-2H-1,3-thiazin-2-ylidene)acetate (8A) was prepared as a yellow solid, m.p.: 47°-48°, by treating 1A with 2-(octylthio)ethanol according to the procedure described in Example 1.

8 was prepared as a brown liquid, boiling point not determined, by treating 8A with methyl fluorosulfonate according to the procedure described in Example 6.

EXAMPLE 9 dimethyl (2-(nitro(tetrahydro-2H-1,3-thiazin-2-ylidene)acetyloxy)propyl)sulfonium iodide (9)

1-methyl-2-(methylthio)ethyl nitro(tetrahydro-2H-1,3-thiazin-2-ylidene)acetate (9A) was prepared as a yellow solid, m.p.: 58°-60°, by treating 1A with 2-(methylthio)-2-methylethanol according to the procedure described in Example 1.

9 was prepared as a yellow solid, m.p.: 113°-114°, by treating 9A with methyl iodide according to the procedure described in Example 1.

EXAMPLE 10 dimethyl(1-methyl-2-(nitro(tetrahydro-2H-1,3-thiazin-2-ylidene)acetate (10)

2-(methylthio)propyl nitro(tetrahydro-2H-1,3-thiazin-2-ylidene)acetate (10A) was prepared as a yellow solid, m.p.: 34°-38°, by treating 1A with 2-(methylthio)propyl alcohol according to the procedure described in Example 1.

10 was prepared as a yellow solid, m.p.: 108°-109° (with decomposition) by treating 10A with methyl iodide according to the procedure described in Example 1.

The salts of this invention exhibit useful insecticidal activity, being of particular interest for control of the larval "caterpillar" or "worm" forms of lepidopterous insects of the genus Heliothis, such as *H. zea* (corn earworm, cottom bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm). In tests that have been conducted, all ten compounds exhibited low, or no, toxicity to other insects such as houseflies, aphids, 2-spotted spider mites and mosquito larvae. Six act very rapidly with respect to corn earworms, providing "quick knock-down" of this lepidopterous insect.

Activity of the compounds of this invention with respect to insects was determined by using standardized test methods to establish the LC$_{50}$ dosage (in milligrams of test compound per 100 milliliters of solvent or liquid carrier required in the solution or suspension of test compound used) that was required to kill 50% of the test insects. The test insects were the housefly, corn earworm, mosquito larvae, pea aphid and 2-spotted spider mite.

All of the compounds 1 through 10 were found to be inactive or but slightly active with respect to the mites and mosquito larvae. With respect to the corn earworm all ten compounds were found to be active. With respect to the pea aphid compound 4 was found to be slightly active. Compounds 1 through 7 were found to have slight to low activity with respect to houseflies.

In the course of these tests it was noted that compound 4 acted very quickly on houseflies while compounds 1-4 and 6-7 acted very quickly on corn earworms.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material, which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the salts of this invention and liquids in which the toxicant is insoluble or only slightly soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils; chlorinated hydrocarbons, such as carbon tetrachloride, perchlorethylene, trichloroethane; including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated castor oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerolsols. Encapsulated formulations and conrolled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10%w of active ingredient. Granules may be manufactured by agglomeration or impregnation techniques. Generally, granules will contain ½-25%w active ingredient and 0-10%w of additives such as stabilizers, slow release modifiers and binding agents. Emulsifiable concentrates usually contain, in addition to the solvent, and when necessary, co-solvent, 10-50%w/v active ingredient, 2-20%w/v emulsifiers and 0-20%w/v of appropriate additives such as stabilizers, penetrants and corrosion inhibitors. Suspension concentrates are compounded so as to obtain a stable, non-sedimenting, flowable product and usually contain 10-75%w active ingredient, 0-5%w of dispersing agents, 0.1-10%w of suspending agents such as protective colloids and thixotropic agents, 0-10%w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of the active ingredient at the locus being within the skill of those versed in the art. In general, however, the effective dosage of salts of this invention at the locus to be protected — i.e. the dosage to which the insect contacts — is of the order of 0.001% to 0.5% based on the total weight of the formulation, though under some circumstances the effective concentration will be as little as 0.001% or as much as 2%, on the same basis.

What is claimed is:

1. A sulfonium salt of the formula:

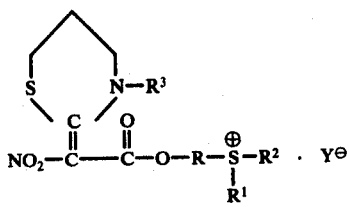

wherein Y is an anion selected from chloride, bromide, iodide, methyl sulfate, fluorosulfonyl and fluoborate, R is —$CH_2$—$CH_2$— or such in which one of the hydrogen atoms has been replaced by methyl, $R^1$ is alkyl of 1 to 3 carbon atoms, $R^2$ contains up to twenty carbon atoms and is alkyl or alkenyl or is phenyl, benzyl or phenethyl, and $R^3$ is hydrogen or

wherein Z is —$R^4$, —$OR^4$ or —$SR^4$, $R^4$ being one of the moieties represented by $R^2$.

2. A salt according to claim 1 wherein $R^1$ is methyl, $R^2$ is alkyl or from one to fifteen carbon atoms or is phenyl, $R^3$ is hydrogen, alkanoyl or alkoxycarbonyl of from one to ten carbon atoms or is benzoyl.

3. A salt according to claim 2 wherein $R^2$ is alkyl, $R^3$ is hydrogen or benzoyl and Y is bromide or iodide.

4. A method for controlling insects which comprises contacting them with an insecticidally effective amount of a salt of claim 1.

5. An insecticidal composition comprising an insecticidally effective amount of a salt of claim 1 together with an insecticidal adjuvant therefor.

* * * * *